(12) United States Patent
Schaller et al.

(10) Patent No.: US 10,322,029 B2
(45) Date of Patent: Jun. 18, 2019

(54) OCULAR IMPLANT CONTAINER

(71) Applicant: Novartis AG, Basel (CH)

(72) Inventors: Michael Paul Schaller, Menlo Park, CA (US); David Reza Lari, Menlo Park, CA (US); Luke William Clauson, Menlo Park, CA (US)

(73) Assignee: Novartis AG, Basel (CH)

( * ) Notice: Subject to any disclaimer, the term of this patent is extended or adjusted under 35 U.S.C. 154(b) by 293 days.

(21) Appl. No.: 15/268,305

(22) Filed: Sep. 16, 2016

(65) Prior Publication Data

US 2017/0079839 A1  Mar. 23, 2017

Related U.S. Application Data

(60) Provisional application No. 62/221,918, filed on Sep. 22, 2015.

(51) Int. Cl.
*A61F 9/00* (2006.01)
*A61M 25/09* (2006.01)
*A61F 2/16* (2006.01)

(52) U.S. Cl.
CPC .......... *A61F 9/0017* (2013.01); *A61F 2/1662* (2013.01); *A61M 25/09* (2013.01); *A61F 2250/0068* (2013.01)

(58) Field of Classification Search
CPC ...... A61F 9/0017; A61F 9/0026; A61F 9/007; A61F 9/00727; A61F 9/00781; A61F 2/1662; A61F 2/16; A61F 2250/00687; A61M 27/002; A61M 25/09
IPC ..................................................... A61F 9/0017
See application file for complete search history.

(56) References Cited

U.S. PATENT DOCUMENTS

| | | |
|---|---|---|
| 5,180,362 A | 1/1993 | Worst |
| 8,337,393 B2 | 12/2012 | Silverstrini et al. |
| 8,377,122 B2 | 2/2013 | Silvestrini et al. |
| 8,444,589 B2 | 5/2013 | Silvestrini |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,617,139 B2 | 12/2013 | Silvestrini et al. |
| 8,672,870 B2 | 3/2014 | Silvestrini et al. |
| 8,851,676 B2 | 10/2014 | John et al. |
| 9,084,662 B2 | 7/2015 | Gifford, III et al. |
| 9,241,832 B2 | 1/2016 | Schaller et al. |
| 9,480,598 B2 | 11/2016 | Clauson et al. |
| 9,763,829 B2 | 9/2017 | Clauson et al. |
| 9,788,999 B2 | 10/2017 | Schaller |
| 9,987,163 B2 | 6/2018 | Schaller |
| 10,085,633 B2 | 10/2018 | Schaller et al. |
| 10,154,924 B2 | 12/2018 | Clauson et al. |

(Continued)

FOREIGN PATENT DOCUMENTS

| | | |
|---|---|---|
| CN | 101969898 A | 2/2011 |
| CN | 104540472 A | 4/2015 |

(Continued)

*Primary Examiner* — Philip R Wiest
(74) *Attorney, Agent, or Firm* — Mintz Levin Cohn Ferris Glovsky and Popeo, P.C.

(57) ABSTRACT

An implant container for containing an ocular implant is described herein. The implant container can releasably couple to an implant delivery device and provide at least partial alignment of the delivery device with an ocular implant during loading of the ocular implant onto the delivery device.

19 Claims, 8 Drawing Sheets

(56) References Cited

U.S. PATENT DOCUMENTS

| | | | |
|---|---|---|---|
| 2004/0147870 A1* | 7/2004 | Burns | A61F 9/0017 604/8 |
| 2006/0142780 A1* | 6/2006 | Pynson | A61F 2/1662 606/107 |
| 2010/0134759 A1 | 6/2010 | Silvestrini et al. | |
| 2011/0105990 A1 | 5/2011 | Silvestrini | |
| 2011/0118835 A1 | 5/2011 | Silvestrini et al. | |
| 2011/0264102 A1 | 10/2011 | Cole et al. | |
| 2014/0309599 A1 | 10/2014 | Schaller | |
| 2014/0323995 A1 | 10/2014 | Clauson et al. | |
| 2015/0238687 A1* | 8/2015 | Novakovic | A61M 5/158 604/502 |
| 2016/0346125 A1 | 12/2016 | Coroneo | |
| 2018/0071143 A1 | 3/2018 | Silvestrini et al. | |
| 2018/0092775 A1 | 4/2018 | de Juan, Jr. et al. | |
| 2018/0104103 A1 | 4/2018 | Yablonski | |
| 2018/0256397 A1 | 9/2018 | Schaller et al. | |

FOREIGN PATENT DOCUMENTS

| | | |
|---|---|---|
| CN | 104755046 A | 7/2015 |
| CN | 104814810 A | 8/2015 |
| WO | WO-2007087641 A2 | 8/2007 |

* cited by examiner

OCULAR IMPLANT CONTAINER

CROSS-REFERENCE TO RELATED APPLICATION

The current application claims priority to U.S. Provisional Patent Application Ser. No. 62/221,918 filed on Sep. 22, 2015 and entitled "OCULAR IMPLANT CONTAINER," which is incorporated by reference herein in its entirety.

TECHNICAL FIELD

The subject matter described herein relates to an implant container that can contain an ocular implant and assist with loading the ocular implant onto an implant delivery tool.

BACKGROUND

During implantation of some ocular implants, a delivery tool is used for guiding the ocular implant to a desired implantation site. The delivery tool may be comprised of any number of mechanisms for securing or holding the ocular implant during the surgical procedure. For example, some delivery tools have a guidewire that extends through a lumen of an implant and constrains the implant, which can enable the user to guide the implant to the implantation site. The guidewire may include additional retention features for securing the implant onto the guidewire, such as frictional features or the like. In other delivery devices, a sheath or cover over the implant may be used for constraining the implant. Other delivery devices may use a gripping mechanism to hold a distal edge or any other section of the implant during the procedure.

An important step of the surgical procedure can be connecting the implant to a holding mechanism of the delivery tool. For example, in the case of a guidewire holding mechanism, the implant lumen is relatively aligned with the guidewire such that the guidewire can be inserted into the lumen of the implant. The implant can be manually held in a position that maintains this relative alignment during the loading. In other holding mechanisms, similar requirements exist.

The user may hold the implant with their hand and insert it onto the guidewire, but this presents several challenges. Ocular implants are generally small and the lumen and associated guidewire are also small so the features may be difficult to see clearly and to handle manually. If the necessary features are not properly aligned the guidewire may damage the implant, such as near the lumen, causing a device defect or failure.

Alternatively, the manufacturer may supply to the user the delivery tool with the implant already loaded. However, this may have a negative impact on the implant or the delivery tool depending on certain factors. For example, the implant may be made of materials that can be altered or damaged during continuous contact with the guidewire or other parts of the delivery tool. For example, during sterilization cycles or shipping the implant may be subjected to forces or loads by the delivery tool that are unwanted and cause a change in the implant.

SUMMARY

Aspects of the current subject matter include embodiments of an implant container configured to contain an ocular implant and assist with loading the ocular implant onto an implant delivery tool. In some implementations, the implant container can include a housing having a proximal end configured to couple to an implant delivery device. The implant container can further include an implant positioner integrated with the housing and configured to align and releasably secure an ocular implant for loading onto the implant delivery device.

In some variations, one or more of the following features can optionally be included in any feasible combination. The aligning of the ocular implant can include aligning a lumen of the ocular implant with a delivery feature of the implant delivery device. The implant positioner can include a chamber enclosed within the housing and in communication with a delivery passageway extending between the chamber and the proximal end of the housing. The delivery passageway can allow a delivery feature of the implant delivery device to extend therethrough for loading the ocular implant onto the delivery feature. The delivery passageway can have a diameter that allows the delivery feature with the loaded ocular implant to translate therealong and exit the housing when the housing is uncoupled from the implant delivery device. The delivery feature can include at least one of a hypotube and a guidewire. The implant container can further include a coupling feature at the proximal end of the housing configured to at least one of releasably couple to the implant delivery device and align a delivery feature of the implant delivery device with the implant positioner for loading the ocular implant onto the delivery feature. The coupling feature can axially constrain the implant container relative to the implant delivery device. The coupling feature can include at least one retention arm extending from the proximal end of the housing and include a cammed surface configured to releasably couple to a securing feature of the implant delivery device. The implant delivery device can include a releasing feature that decouples the at least one retention arm from the securing feature after the ocular implant is loaded onto the delivery feature. The housing can include a squeeze arm operatively coupled to the at least one retention arm such that when the squeeze arm is depressed, the at least one retention arm is decoupled from the implant delivery device thereby decoupling the housing from the implant delivery device. The coupling feature can include a recessed cone shape at the proximal end of the housing, and the recessed cone shape can provide a sliding fit with a distal end of the implant delivery device. The coupling feature can include a pin configured to engage a threaded feature of the implant delivery device thereby coupling the housing to the implant delivery device. The chamber can include a fluid comprising one or more of a saline solution and a therapeutic drug. A part of the housing can be made out of a translucent material that allows a user to view the ocular implant in the chamber. The translucent material can include a magnification property that enlarges an image of the ocular implant in the chamber.

In another aspect, a method can include loading an ocular implant into an implant positioner of an implant container. The implant container can include a housing configured to couple to an implant delivery device for loading the ocular implant onto the implant delivery device and align the ocular implant with a delivery feature of the implant delivery device when the housing is coupled to the implant delivery device. The method can further include coupling the housing of the implant container to the implant delivery device thereby aligning the delivery feature of the implant delivery device with the ocular implant, loading the ocular implant onto the delivery feature, and decoupling the housing from the implant delivery device thereby removing the ocular implant loaded onto the delivery feature from the implant container. The loading of the ocular implant onto the implant delivery device can include longitudinally translating a guidewire into a lumen of the ocular implant. The method can further include activating a decoupling feature associated with at least one of the implant container and the implant delivery device to cause the decoupling of the housing from the implant delivery device.

In another aspect, a system can include an implant delivery device, an ocular implant, and an implant container. The implant container can include a housing having a proximal end configured to couple to the implant delivery device and an implant positioner integrated with the housing and configured to align and releasably secure the ocular implant for loading onto the implant delivery device.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Described herein is an implant container for positioning an ocular implant relative to a delivery feature of an implant delivery device and assisting loading the ocular implant onto the delivery feature. Such positioning provided by the container device improves loading of the ocular implant onto the delivery feature by preventing misalignment of the implant during loading. This can improve the efficiency of a procedure and reduce or eliminate damage to the implant. For example, if the implant is misaligned with the delivery feature during loading, the delivery feature can damage (e.g., puncture, tear) the implant. Furthermore, since the size of ocular implants are small and difficult to load onto a delivery device, the implant container provides an efficient and safe way to load an ocular implant onto a delivery device, thus saving time and money during a procedure.

Various embodiments of an implant container are described herein that can be coupled to (including integrated with) a delivery tool while also not requiring any positioning of the implant by the user prior to loading the implant. Some embodiments of an implant container can be similar to a pen cap that is held on the end of a delivery tool for properly constraining and aligning the implant during the loading procedure.

Many ophthalmic implants are small (on the order of millimeters) and difficult to handle manually. Such ophthalmic implants can require loading of the implant onto a delivery tool, a method whereby a user can manually place the implant onto a separate accessory device that is used for placing the implant at time of surgery. An approach to implant loading that requires minimal amount of user handling and potential for implant damage or misuse (i.e. placing backwards, placing debris on implant, etc.) can reduce surgery time, streamline procedures, and minimize implant loading related complications. An implant container, whereby an implant is positioned and aligned relative to a delivery device such that loading may be done with minimal operator handling is one approach that makes use of such benefits.

Figure 1:
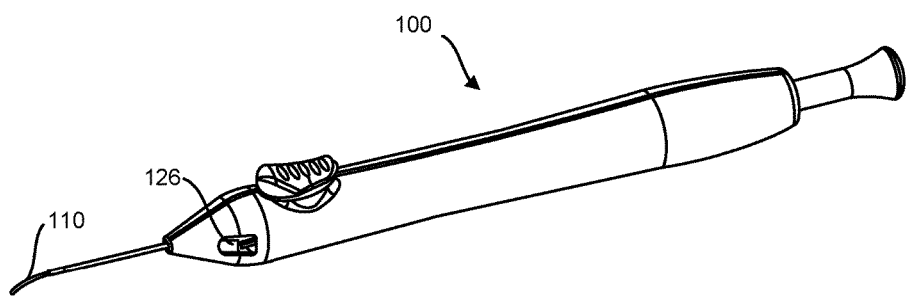
FIG. 1 illustrates an isometric view of a delivery tool consistent with implementations of the current subject matter.
Figure 2:
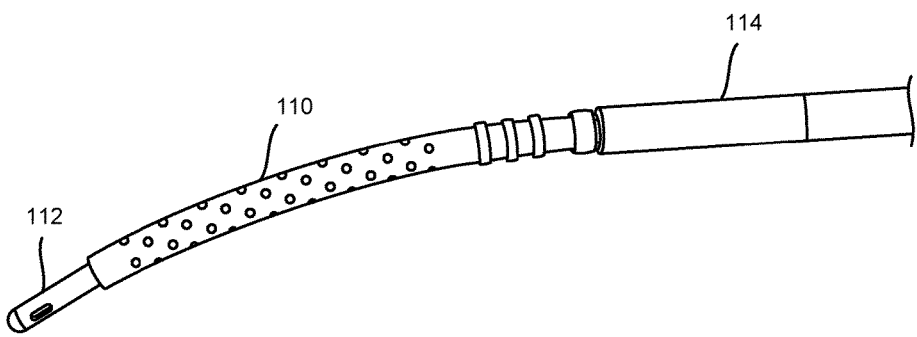
FIG. 2 illustrates a partial side view of the distal end of the delivery tool of FIG. 1 with an ocular implant loaded thereon.

FIG. 1 shows a delivery tool 100 with an implant 110 loaded on a guidewire 112 extending from a distal end of the delivery tool 100. FIG. 2 shows the distal end of the delivery tool 100 of FIG. 1 in greater detail. The implant 110 is loaded onto the guidewire 112 and abutted against a hypotube 114. In this example, the guidewire 112 extends beyond the distal end of the implant 110, however, any length of guidewire 112 may be considered for the inventive device described herein.

Figure 3:
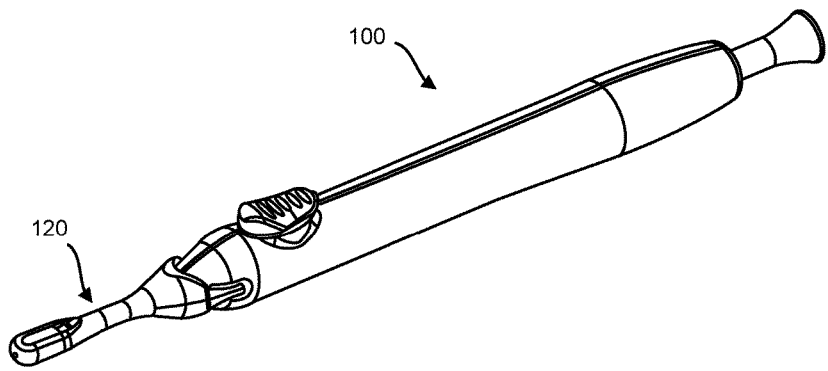
FIG. 3 illustrates an isometric view of the delivery tool of FIG. 1 with an embodiment of an implant container coupled to a distal end of the delivery tool.

In FIG. 3, an embodiment of an implant container 120 is shown coupled to the distal end of the delivery tool 100. The implant container 120 can releasably secure the implant 110 in a position such that a lumen of the implant is aligned with a delivery feature (e.g., hypotube 114 and/or guidewire 112) of the delivery tool 100. The implant container 120 in this embodiment is similar to a pen cap that is integrated onto the end of the delivery device 100. The implant container 120 provides several functions such as holding the implant 110 in the correct orientation and alignment during the loading procedure (e.g., loading the implant 110 onto the guidewire 112 extending from the distal end of the delivery tool 110). The implant container 120 may also protect the implant 110 during shipping, surgical preparation, and user interaction before the loading procedure begins.

Figure 4:
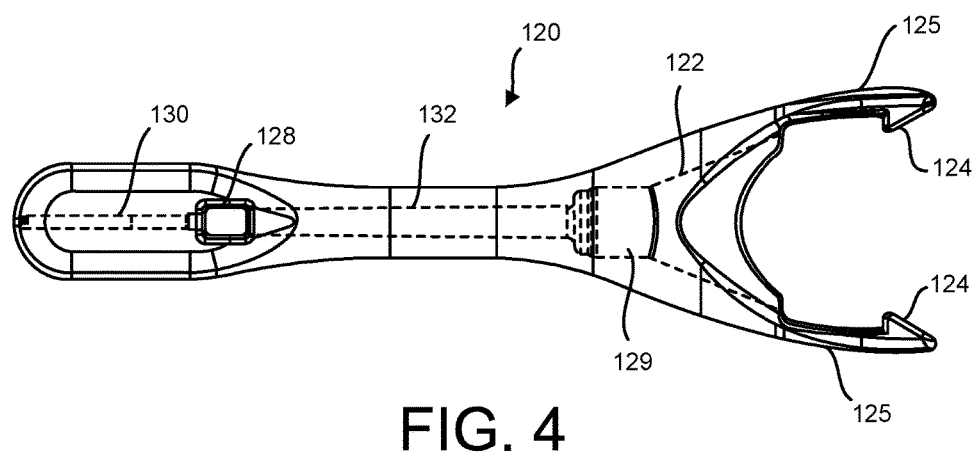
FIG. 4 illustrates a top view of the implant container shown in FIG. 3.

In FIG. 4, the implant container 120 of FIG. 3 is shown. The implant container 120 may have an implant positioner or housing 130 that constrains the implant 110. The implant housing 130 may be sized to be slightly larger than the size of the implant 110 so that the implant 110 is held in place. Alternatively, the implant housing 130 may be slightly smaller than the implant 110 in one or more dimensions to provide a friction fit. In some embodiments, the implant housing 130 includes a chamber enclosed within a housing of the implant container 120 and in communication with a delivery passageway 132 that extends between the chamber and a proximal end of the container housing. The delivery passageway 132 can be sized to allow the delivery feature of the implant device with the implant loaded thereon to travel along the delivery passageway 132 to exit the implant container 120 when the implant container 120 is decoupled from the delivery device 100. In some embodiments, the implant container 120 may simply have a single feature that holds the implant 110, such as a loop or a spring clip, and the rest of the implant 110 may not be surrounded by material.

The implant container 120 can contain features that interface with the delivery device 100. For example, the delivery passageway 132 can assist with securing alignment between the delivery feature (e.g., hypotube 114 and/or guidewire 112) and the implant 110. For example, the hypotube 114 and the delivery passageway 132 can have a cylindrical cross-section and the delivery passageway 132 can provide a sliding or near-sliding fit with the hypotube thereby axially constrain the implant container 120 to the delivery device 100 when the hypotube 114 extends along the delivery passageway 132. Additionally, features may be added to the hypotube 114 that further allow for alignment and orientation of the implant container 120 relative to the delivery device 100. For example, cut features on the hypotube 114 or bosses extending out of the hypotube 114 may be used for alignment of the implant container 120 to the delivery device 100.

In some embodiments, the implant container 120 can interface with a handle component of the delivery device 100. The implant container 120 may have a feature such as a conical hole 122 that aligns with a conical feature 123 (see, for example, FIGS. 5 and 6) on the handle, which properly aligns and locates the implant container 120 relative to the delivery device 100. Any number of other features or components may be contemplated for interfacing the delivery tool 100 to the implant container 120.

In some embodiments, the implant container 120 can be securely held onto the distal end of the delivery device 100 like a pen cap. In this embodiment, the implant container 120 may contain one or more coupling features that releasably couple the implant container 120 to the delivery device 100. In FIG. 4, the implant container 120 includes a pair of retention arms 125 that extend from a proximal end of the implant container 120 and are configured to engage with one or more coupling features 126 (e.g., groove, recess) on the delivery device 100 (see, for example, FIG. 1). The retention arms 125 may include cam surfaces 124 (see, for example, FIG. 11) that can be decoupled from the coupling feature 126 at the end of the loading procedure. Such decoupling can be caused by a feature associated with the delivery device 100 in order to eject the implant container 120 off the delivery device 100 after loading of the implant 110 onto the delivery feature of the delivery device 100. The implant container 120 may include a spring housing 129 that holds a spring that can be pressed against the front surface of the delivery tool 100 such that when the retention arms 125 are cammed out or decoupled from the delivery device 100, the implant container 120 is ejected off of the delivery device 100. In other embodiments, other force mechanisms such as elastic deformation of the retention arms 125 may be used for ejecting the implant container 120.

In other embodiments, the implant container 120 may not include or require retention features for holding the implant container 120 against the delivery tool 100. The implant container 120 can include alignment features to allow the user to properly align the implant 110 and the delivery tool 100 before beginning the loading procedure.

The implant container 120 may be manufactured from translucent or opaque plastics (i.e. polycarbonate, ABS, polypropylene, etc.), metals (i.e. stainless steel, titanium, etc.), or other equivalent materials. The use of translucent plastics may allow the user to see the implant 110 in the implant housing 130, including during the loading procedure. Alternatively, one or more windows 128 may be included in the implant container 120 to allow the user to see the implant 110, such as during the loading procedure. In still other embodiments, the translucent plastic may be configured in such a way to magnify or enlarge an image of the implant during the loading procedure to make certain areas and features more visible.

In some implementations, the implant container 120 consists of a single part comprised of injection molded plastic. In other embodiments, the implant container 120 may be comprised of any number of components secured together as an assembly. Furthermore, the components may be stationary relative to one another or move relative to one another such as telescoping components or features.

Figure 5:
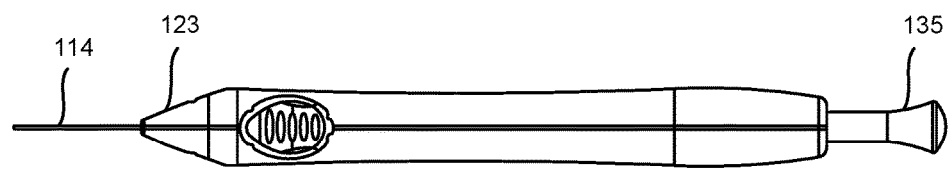
FIG. 5 illustrates a top view of the delivery tool of FIG. 1.
Figure 6:
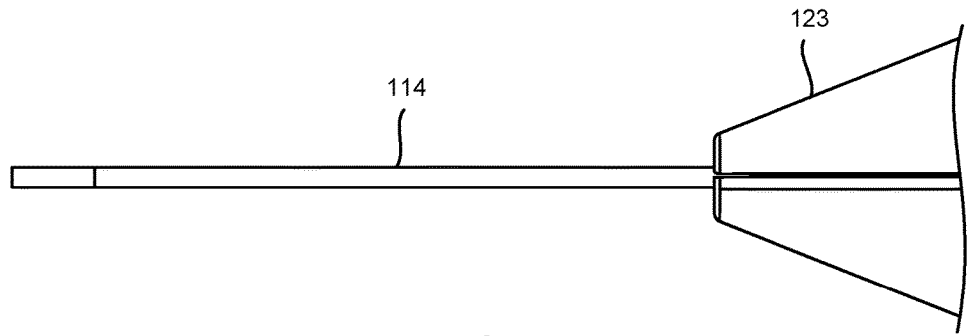
FIG. 6 illustrates a partial side view of the distal end of the delivery tool of FIG. 5.

Turning now to FIGS. 5-9, a loading procedure with a delivery tool 100 is shown. In FIG. 5, a top view of a delivery tool 100 is shown with a loading button 135 at the proximal end and a hypotube 114 at the distal end. The delivery tool 100 can include a variety of handle components. In FIG. 6, the distal end of the delivery tool 100 is shown in greater detail. The hypotube 114 may include a lumen that allows a guidewire to extend therethrough. As discussed in greater detail below, the guidewire can extend out of the hypotube 114 and retract into the hypotube 114.

Figure 7:
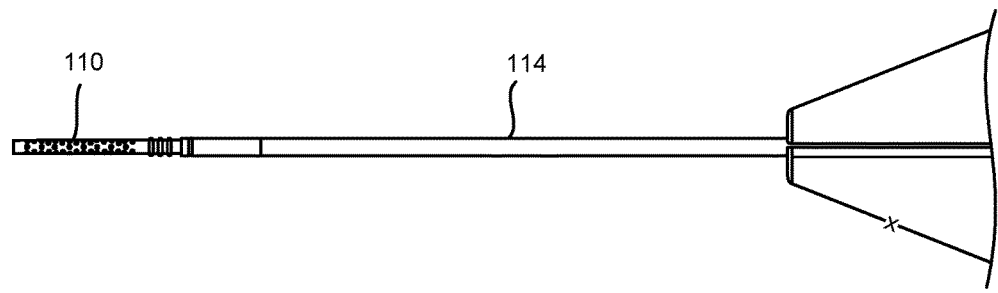
FIG. 7 illustrates a partial top view of the distal end of the delivery tool of FIG. 6 with an ocular implant aligned with the distal end before loading the implant onto either the delivery tool or guidewire.

In FIG. 7, an implant 110 is shown in relation to the delivery tool 100. The lumen of the implant 110 is generally aligned with the axis of the hypotube 114 and when the guidewire 112 is extended it will enter the lumen of the implant 110 thereby loading the implant 110 onto the delivery tool 100. One of the functions of the container device 120 described herein is to align the implant 110 with the delivery tool 100, such as with a delivery feature (e.g., hypotube 114, guidewire 112) of the delivery tool 100, and reduce the amount of user input required to align and load the implant 110.

Figure 8:
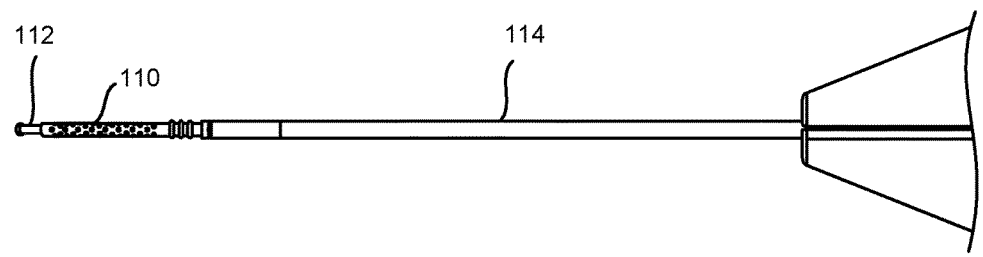
FIG. 8 illustrates a partial top view of the distal end of the delivery tool of FIG. 6 with the ocular implant loaded onto a guidewire extending from the distal end of the delivery tool.
Figure 9:
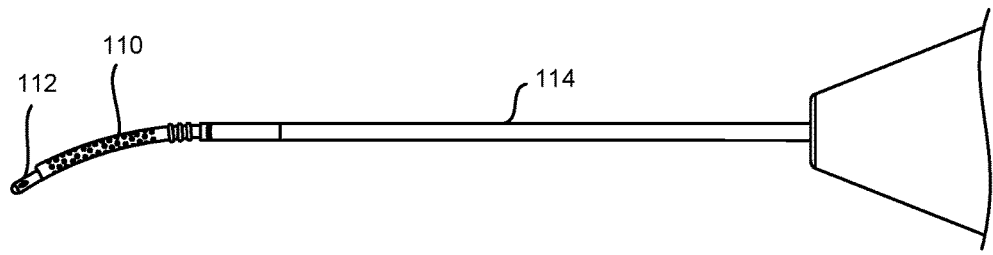
FIG. 9 illustrates a side view of the distal end of the delivery tool of FIG. 6 with an implant loaded onto a guidewire extending from the distal end of the delivery tool.

In FIG. 8, the guidewire 112 is extended through the lumen in the implant 110 and shown from a top view. As discussed above, any number of other holding mechanisms may be contemplated for securing the implant 110 to the delivery device 100. In FIG. 9, the delivery tool 100 and implant 110 are shown from a side view. The guidewire 112 may have a curve or bend that causes the implant 110 to curve or bend. Alternatively, the implant 110 may have a curve or bend that causes the guidewire 112 to curve or bend.

Figure 10:
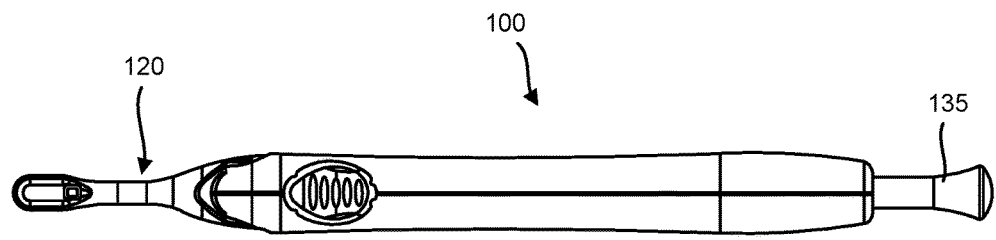
FIG. 10 illustrates a top view of the delivery tool of FIG. 1 with an implant container coupled to a distal end of the delivery tool.

In FIG. 10, the implant container 120 is shown coupled to the delivery tool 100 during the loading procedure. The proximal end of the implant container 120 can be releasably coupled to the distal end of the delivery tool 100, as shown in FIG. 10.

Figure 11:
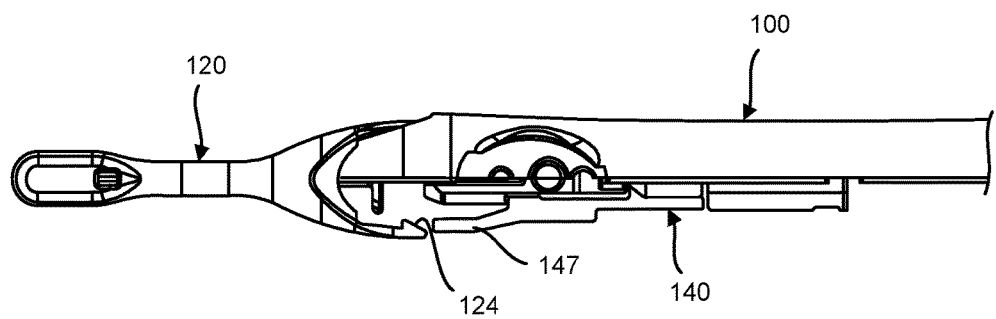
FIG. 11 illustrates a top down view of a delivery tool and integrated implant container with a portion of the handle of the delivery tool hidden.

In FIG. 11, the implant container 120 is shown in greater detail with half of the handle of the delivery tool 100 removed thereby showing one of the retention arms 125 extending along the delivery device 100. The retention arms 125 are shown and can engage with a feature on the handle thereby securely mating the implant container 120 to the delivery tool 100, including during shipping and loading. An internal component shown is a piston 140. The piston 140 may be connected to other components such as the guidewire 112 such that by sliding the piston 140 distally, the guidewire 112 extends from the hypotube 114 and the implant 110 is loaded onto the guidewire 112. In such an embodiment, the piston 140 can be translated by pressing the loading button 145 on the proximal end of the delivery tool. As the loading button 135 is depressed, the piston 140 translates distally and the guidewire 112 is extended distally (e.g., toward the implant 110). As shown in FIG. 11, the piston 140 may include piston cam arms 147 at the distal end that are configured to engage with the retention arms 125. As the piston cam arms 147 translate distally they can release the coupling between the retention arms 125 and the securing feature 126 thus allowing the implant container 120 to be ejected or removed from the delivery tool 100. In such an embodiment, the timing of the loading and the ejection of the implant container 120 may be timed such that ejection occurs after the loading of the implant 110 onto the guidewire 112. The user presses the loading button 135 and the implant 110 is loaded onto the guidewire 112 and the implant container 120 is actively or passively removed from the delivery tool 100.

Figure 12:
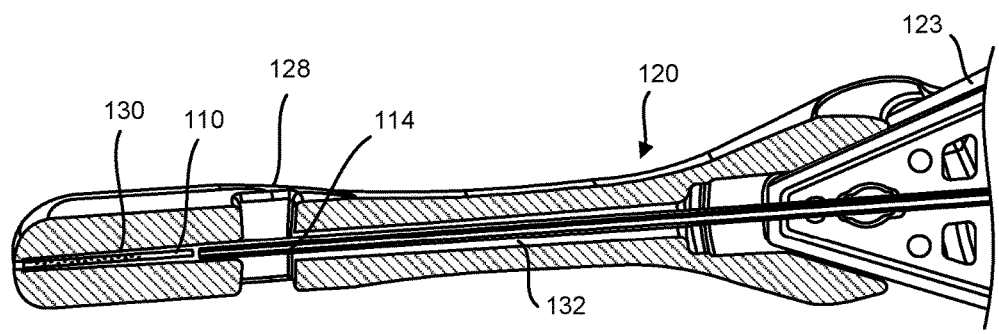
FIG. 12 illustrates a section view of a delivery tool and integrated implant container with the implant in a chamber of the container housing and not loaded onto the delivery device.
Figure 13:
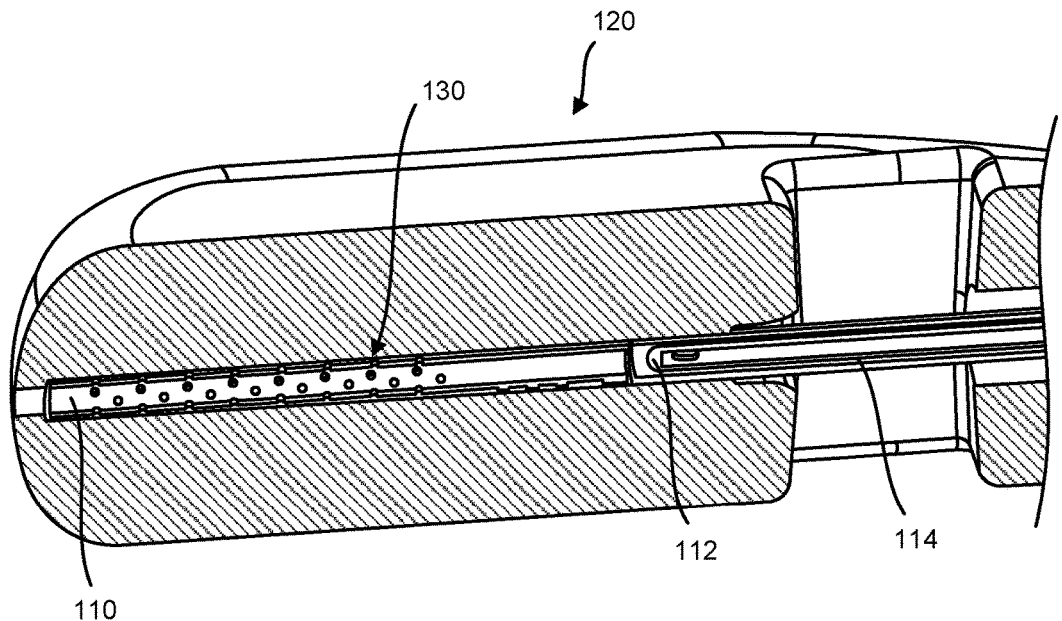
FIG. 13 shows a detailed section view of a delivery tool and integrated implant container with the implant in the chamber of the container housing and not loaded onto the delivery device.

In FIG. 12, a section view of the implant container 120 is shown. In FIG. 13, a more detailed view of the implant 110 within the chamber or implant housing 130 of the implant container 120 is shown. The implant housing 130, as well coupling and alignment features associated with the housing of the implant container 120, holds the implant concentrically with the hypotube and the guidewire. The guidewire in FIG. 12 is shown retracted within the lumen of the hypotube. The implant 110 in FIG. 12 is constrained in the implant housing 130 such that the lumen of the implant 110 is coaxially aligned with the guidewire 112 and/or hypotube 114. The implant 110 may be under no stress in this configuration or may be held in place with any sufficient amount of force.

Figure 14:
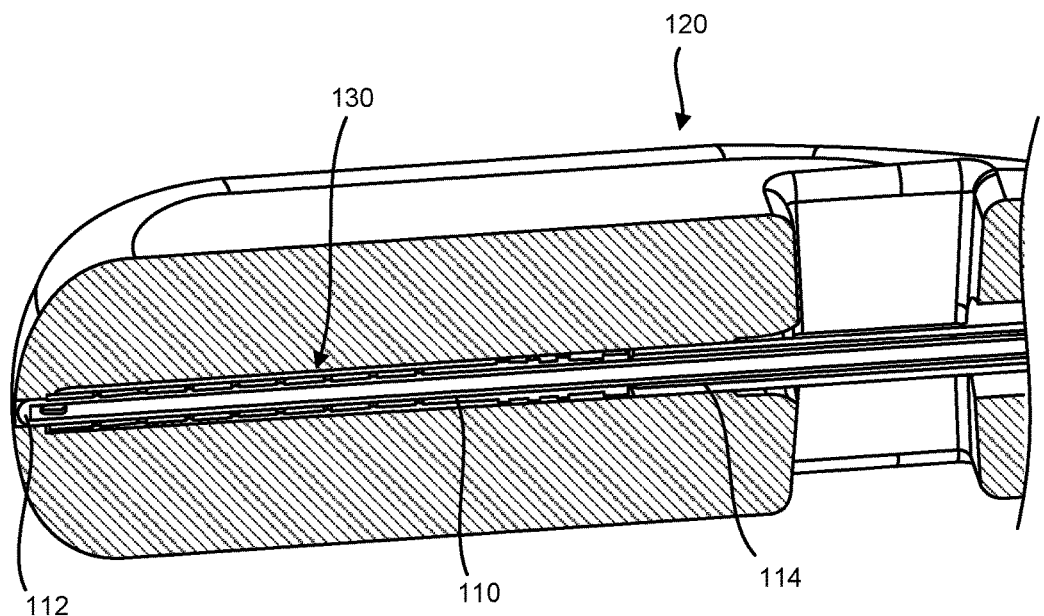
FIG. 14 shows a detailed section view of a delivery tool and integrated implant container with the implant loaded onto a guidewire.

In FIG. 14, the guidewire 112 is shown extended through the lumen of the implant 110. The guidewire 112 may extend beyond the end of the implant 110 or may only extend into a portion of the lumen. The implant 110 is shown loaded onto the guidewire 112 and the implant container 120 may now be decoupled from the delivery device 100.

Figure 15:
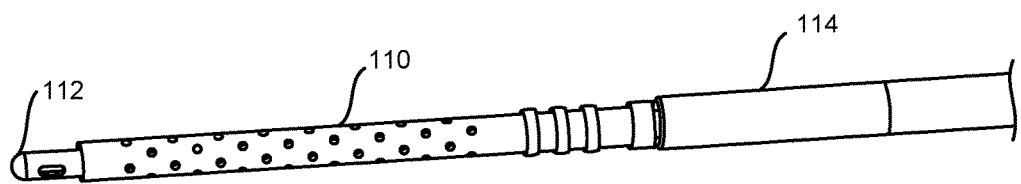
FIG. 15 shows a detailed view of the distal end of a delivery tool with an implant loaded and guidewire straight.
Figure 16:
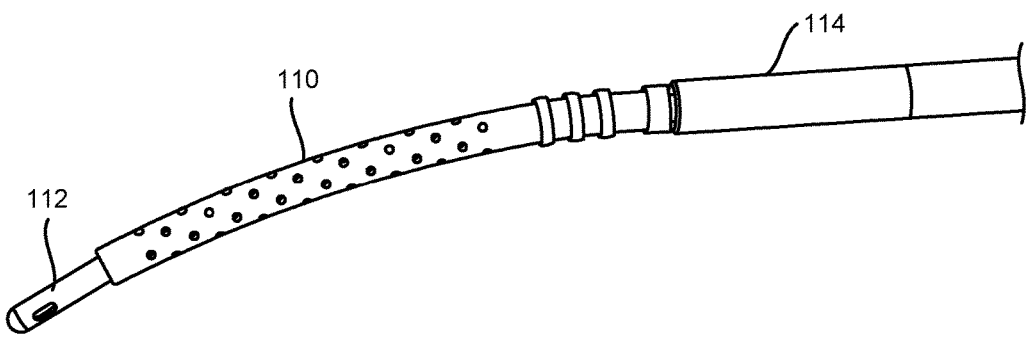
FIG. 16 shows a detailed view of the distal end of a delivery tool with an implant loaded and guidewire curved.

In FIG. 15, the implant 110 loaded onto the guidewire 112 and delivery device 100 is shown decoupled from the implant container 120. In this embodiment, the guidewire 112 is shown straight. In FIG. 16, the implant 110 and guidewire 112 are shown having a bend or curvature along a length. In this embodiment, the guidewire 112 or the implant 110 or both may have a predetermined bend or curve that resumes its natural shape. In an alternate embodiment, features or mechanisms within the implant container 120 may be used to deform the implant 110 and/or guidewire 112 to induce a curve or other geometry. For example, the implant container 120 may have a mechanism where the user can depress a component that flexes the implant 110 and guidewire 112 to a shape. The shape may be predefined or may be selected by the user depending on the force applied or distance moved. This may allow the user to control the shape of the implant 110 or the delivery tool 100 during the implantation procedure.

Figure 17:
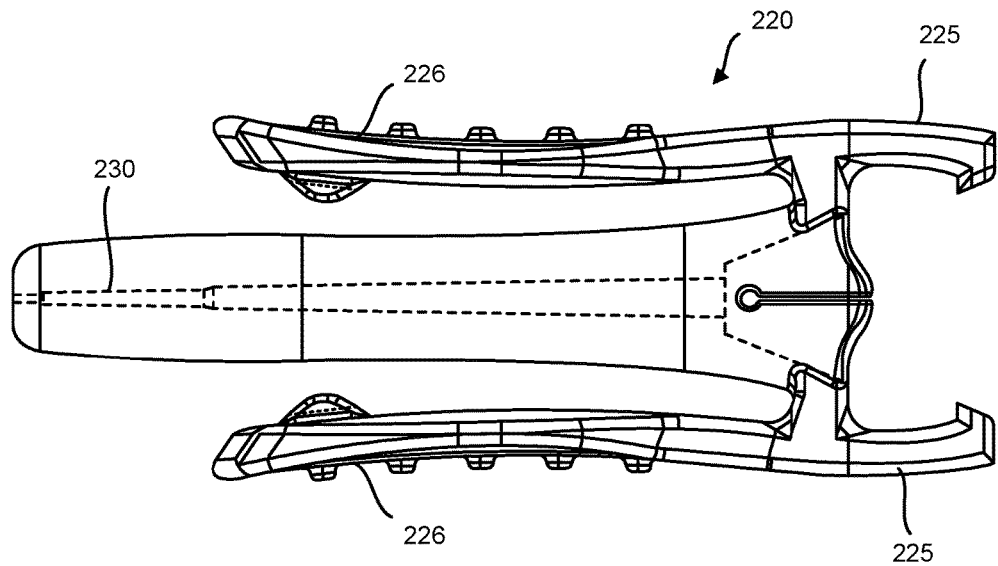
FIG. 17 shows another embodiment of an implant container including a pair of squeeze arms for releasing the coupling between the implant container and a delivery device.
Figure 18:
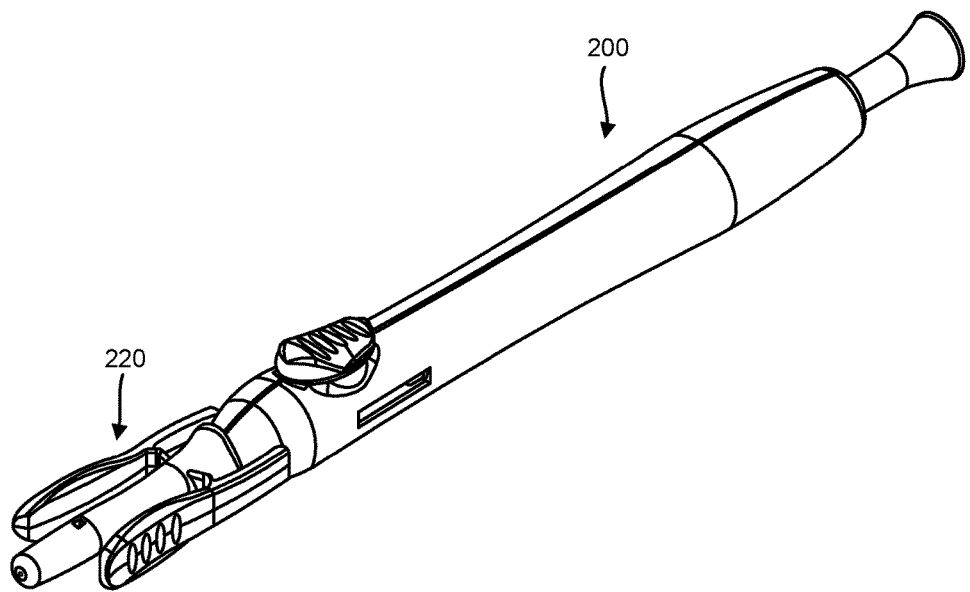
FIG. 18 shows the implant container of FIG. 17 coupled the delivery tool.

In FIG. 17, another embodiment of the implant container 220 is shown including another embodiment of a retention arms 225 that are connected to squeeze arms 226 that may be depressed by the user thereby disengaging the retention arms 225 from a complimenting coupling feature (e.g., groove) along the delivery device 200 to release the implant container 220. In this embodiment, the implant may be loaded into the implant housing 230 for positioning and loading onto the delivery device 200. In FIG. 18, the squeeze arm implant container 220 is shown coupled to the delivery device 200.

Figure 19:
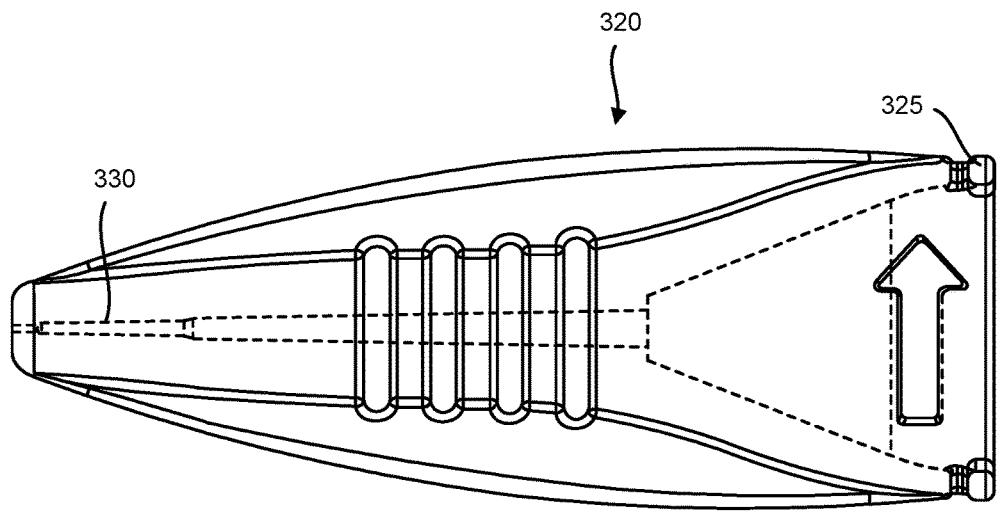
FIG. 19 shows another embodiment of an implant container including a pin that engages and couples to a threaded feature along a delivery device for coupling the implant container to the delivery device.
Figure 20:
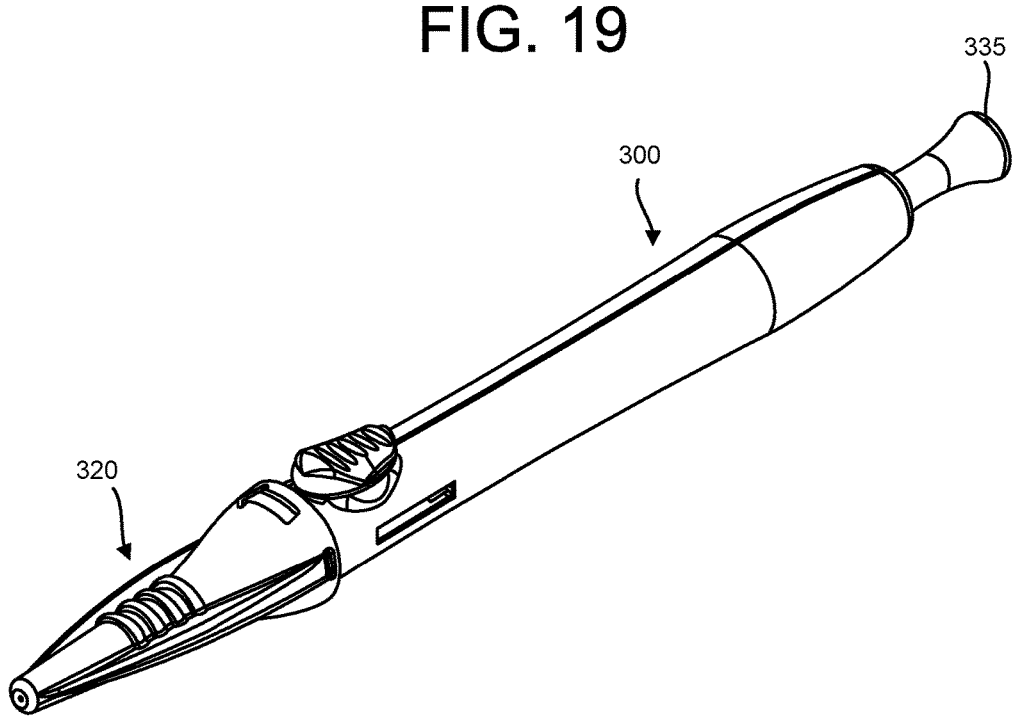
FIG. 20 shows the implant container of FIG. 19 coupled the delivery tool.

In FIG. 19, another embodiment of the implant container 320 is shown having another embodiment of a retention feature, which includes a retention pin 325 which sits into a groove or recess along the delivery tool 300 thereby securely coupling the implant container 320 to the delivery device 300. The groove can be configured like a screw thread that allows the retention pin 325 to thread onto and off of the delivery device 300. The implant 110 can be loaded into the implant housing 330 for positioning and loading the implant 110 onto the delivery device. For example, the guidewire 112 can be advanced into the implant lumen by depressing the loader button 345 and then unthreading the implant container 320 from the delivery device 300 when preparing for surgery.

In some embodiments, the implant 110 may already be loaded onto the delivery device. In these embodiments the implant container (such as implant container 120, 220, and/or 320) may still serve several purposes. First the implant container 120, 220, 320 may protect the implant and prevent any damage from external forces. Second, the implant container 120, 220, 320 may hold the implant 110 in a desired shape or configuration. For example, in the embodiment where the guidewire 112 has a curve at its distal end, the implant container may hold the guidewire straight during the shipping of the device such that the implant is held straight and not subjected to unwanted forces during shipping or storage. In this case the implant container may be removed before the surgical procedure through any number of methods described herein.

In all described configurations, to abut the proximal end of the implant 110 against the distal end of the hypotube 114 during loading, the guidewire 112 may be over-stroked through the implant 110 beyond its final intended position (while features of the container providing a distal hard stop for the implant), resulting in the guidewire 112 pulling the implant 110 proximally (via implant retention features on the guidewire) during its return-stroke with the guidewire hard stopping on the hypotube.

In another embodiment, the implant container may contain features that either permit or prevent re-capping the implant container onto a delivery device. For example, the implant container can irreversibly split into two or more pieces after loading of the implant and removal of the container, thereby not allowing the user to re-cap the container. In another embodiment, the implant container can contain a member that springs to close off the lumen after loading of the implant and removal of the implant container.

The implant container may contain a springing feature that biases the implant proximally, so as to bias the implant towards the correct position during initial loading. In the case of the auto ejecting implant container, various features such as speed bumps on the handle where the retention arm interfaces or a tether connecting the container to the handle body may be used to facilitate the profile of the container's ejection. The implant container design can also include various aerodynamic and friction elements to modify the profile of the container's ejection and minimize the ability to slide along flat surfaces such as tables or floors.

In another embodiment, the implant container may be locked on the delivery tool and cannot be removed with a normal user's hand-grip force until the user has loaded the implant. This is a variation on the embodiments above, where the user actively unlocks or auto ejects the implant container. In this alternative embodiment, the container is not auto ejected, but the only action the user takes to allow the container to be removed is load the implant. Once the implant is loaded, the user can then proceed to remove the container. There can be a change in the container to signal to the user that it is now unlocked and can be removed, such as the appearance of a different color on the delivery tool handle (such as a green label appearing inside of a slot) or in the container itself.

In another embodiment, the implant may be held or contained in a specific environment within the implant container such as a fluid or gaseous environment. This may be beneficial for certain implant materials or configurations. For example, the implant may be maintained in a saline solution and/or a therapeutic drug within the implant container. For example, the chamber or implant housing can be fully are partially sealed to allow the saline and/or therapeutic drug to coat the implant, such as during storage.

In another embodiment, the implant container may be a sheath that holds the implant concentrically on the end of the delivery device and translates toward the delivery device as the implant is inserted in the eye. For example, the implant container can be spring loaded proximally such that it contains the implant at the distal end but is able to move proximally and reveal the implant. In this embodiment, the delivery device can be inserted into the eye and the implant container can be constrained by the corneal incision such that only the implant and the hypotube enter the eye.

In another embodiment, the implant container can contain multiple implants in a series of configurations. The implants can be contained in multiple cavities that are arranged such that the user can enter into a single cavity and load an implant onto the device. The cavities can be linked or unlinked such that they are contained separately and sterility of one implant is unaffected by the sterility of another implant. In this embodiment, the user may use a single implant for one patient and then use a different implant and delivery tool for another patient without compromising sterility.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. The scope of the following claims may include other implementations or embodiments.

What is claimed is:

1. An implant container, comprising:
a housing having a proximal end configured to couple to an implant delivery device; and
an implant positioner integrated with the housing and configured to align and releasably secure an ocular implant for loading onto the implant delivery device, the implant positioner including a first elongated chamber having a first circular cross section defined by a first inner wall configured to provide a friction fit with an outer wall of the ocular implant, the implant positioner further including a second elongated chamber extending between the first elongated chamber and the proximal end of the housing, the second elongated chamber including a second circular cross-section defined by a second inner wall configured to provide a sliding fit with a delivery feature of the implant delivery device, the first elongated chamber and the second elongated chamber being coaxially aligned.

2. The implant container of claim 1, wherein a lumen of the ocular implant is aligned with a guidewire of the delivery feature of the implant delivery device when the ocular implant is positioned in the first elongated chamber and the delivery feature is positioned in the second elongated chamber.

3. The implant container of claim 2, wherein the second elongated chamber has a diameter that allows the guidewire with the loaded ocular implant to translate therealong and exit the housing when the housing is uncoupled from the implant delivery device.

4. The implant container of claim 3, wherein the delivery feature includes a hypotube having an inner lumen configured to allow the guidewire to translate therealong.

5. The implant container of claim 1, further comprising a coupling feature at the proximal end of the housing configured to at least one of releasably couple to the implant delivery device and align the delivery feature of the implant delivery device with the implant positioner for loading the ocular implant onto the delivery feature.

6. The implant container of claim 5, wherein the coupling feature axially constrains the implant container relative to the implant delivery device.

7. The implant container of claim 5, wherein the coupling feature comprises at least one retention arm extending from the proximal end of the housing and includes a cammed surface configured to releasably couple to a securing feature of the implant delivery device.

8. The implant container of claim 7, wherein the implant delivery device includes a releasing feature that decouples the at least one retention arm from the securing feature after the ocular implant is loaded onto the delivery feature.

9. The implant container of claim 7, wherein the housing includes a squeeze arm operatively coupled to the at least one retention arm such that when the squeeze arm is depressed, the at least one retention arm is decoupled from the implant delivery device thereby decoupling the housing from the implant delivery device.

10. The implant container of claim 5, wherein the coupling feature includes a recessed cone shape at the proximal end of the housing, the recessed cone shape providing a sliding fit with a distal end of the implant delivery device.

11. The implant container of claim 5, wherein the coupling feature includes a pin configured to engage a threaded feature of the implant delivery device thereby coupling the housing to the implant delivery device.

12. The implant container of claim 1, wherein the first elongated chamber includes a fluid comprising one or more of a saline solution and a therapeutic drug.

13. The implant container of claim 1, wherein a part of the housing is made out of a translucent material thereby allowing a user to view the ocular implant in the first elongated chamber.

14. The implant container of claim 13, wherein the translucent material includes a magnification property that enlarges an image of the ocular implant in the first elongated chamber.

15. A method, comprising:
loading an ocular implant into an implant positioner of an implant container, the implant container comprising a housing configured to couple to an implant delivery device for loading the ocular implant onto the implant delivery device, the implant positioner configured to align the ocular implant with a delivery feature of the implant delivery device when the housing is coupled to the implant delivery device, the implant positioner including a first elongated chamber having a first circular cross section defined by a first inner wall configured to provide a friction fit with an outer wall of the ocular implant, the implant positioner further including a second elongated chamber extending between the first elongated chamber and the proximal end of the housing, the second elongated chamber including a second circular cross-section defined by a second inner wall configured to provide a sliding fit with a delivery feature of the implant delivery device, the first elongated chamber and the second elongated chamber being coaxially aligned.

16. The method of claim 15, further comprising:
coupling the housing of the implant container to the implant delivery device thereby aligning the delivery feature of the implant delivery device with the ocular implant;
loading the ocular implant onto the delivery feature; and
decoupling the housing from the implant delivery device thereby removing the ocular implant loaded onto the delivery feature from the implant container.

17. The method of claim 16, wherein the loading of the ocular implant onto the implant delivery device comprises longitudinally translating a guidewire into a lumen of the ocular implant.

18. The method of claim 16, further comprising activating a decoupling feature associated with at least one of the implant container and the implant delivery device to cause the decoupling of the housing from the implant delivery device.

19. A system, comprising:
an implant delivery device;
an ocular implant; and
an implant container comprising:
a housing having a proximal end configured to couple to the implant delivery device; and
an implant positioner integrated with the housing and configured to align and releasably secure the ocular implant for loading onto the implant delivery device, the implant positioner including a first elongated chamber having a first circular cross section defined by a first inner wall configured to provide a friction fit with an outer wall of the ocular implant, the implant positioner further including a second elongated chamber extending between the first elongated chamber and the proximal end of the housing, the second elongated chamber including a second circular cross-section defined by a second inner wall configured to provide a sliding fit with a delivery feature of the implant delivery device, the first elongated chamber and the second elongated chamber being coaxially aligned.

* * * * *